United States Patent [19]

Lerner

[11] 3,997,886
[45] Dec. 14, 1976

[54] LIQUID CONTAMINATION DETECTOR

[75] Inventor: Julius Lerner, Broomall, Pa.

[73] Assignee: Sun Oil Company of Pennsylvania, Philadelphia, Pa.

[22] Filed: Sept. 26, 1975

[21] Appl. No.: 616,985

[52] U.S. Cl. .............................. 340/236; 200/61.04; 200/83 B; 210/85; 210/222; 340/242

[51] Int. Cl.² .................... G08B 21/00; B03C 1/30; H01H 35/00

[58] Field of Search .......... 340/239 R, 239 F, 242, 340/236; 200/61.04, 83 B, 83 L; 210/222, 85, 86

[56] References Cited
UNITED STATES PATENTS 2,067,440  1/1937  Finney ................................ 340/242

Primary Examiner—John W. Caldwell
Assistant Examiner—Daniel Myer
Attorney, Agent, or Firm—J. Edward Hess; Donald R. Johnson; William C. Roch

[57] ABSTRACT

A system for detecting the presence of a contaminating fluid in other, normal fluids. In one embodiment the system detects the presence of hydrocarbons in a liquid which is normally water. A barrier which is soluble in hydrocarbons but insoluble in water has one side in contact with the liquid. A liquid sensitive switch is positioned on the other side of the barrier. If hydrocarbons are present, they will dissolve the barrier and close the switch which will set off an alarm. In a second embodiment wherein water is the possible contaminant in hydrocarbons, a barrier which is soluble in water but insoluble in hydrocarbons is utilized.

2 Claims, 3 Drawing Figures

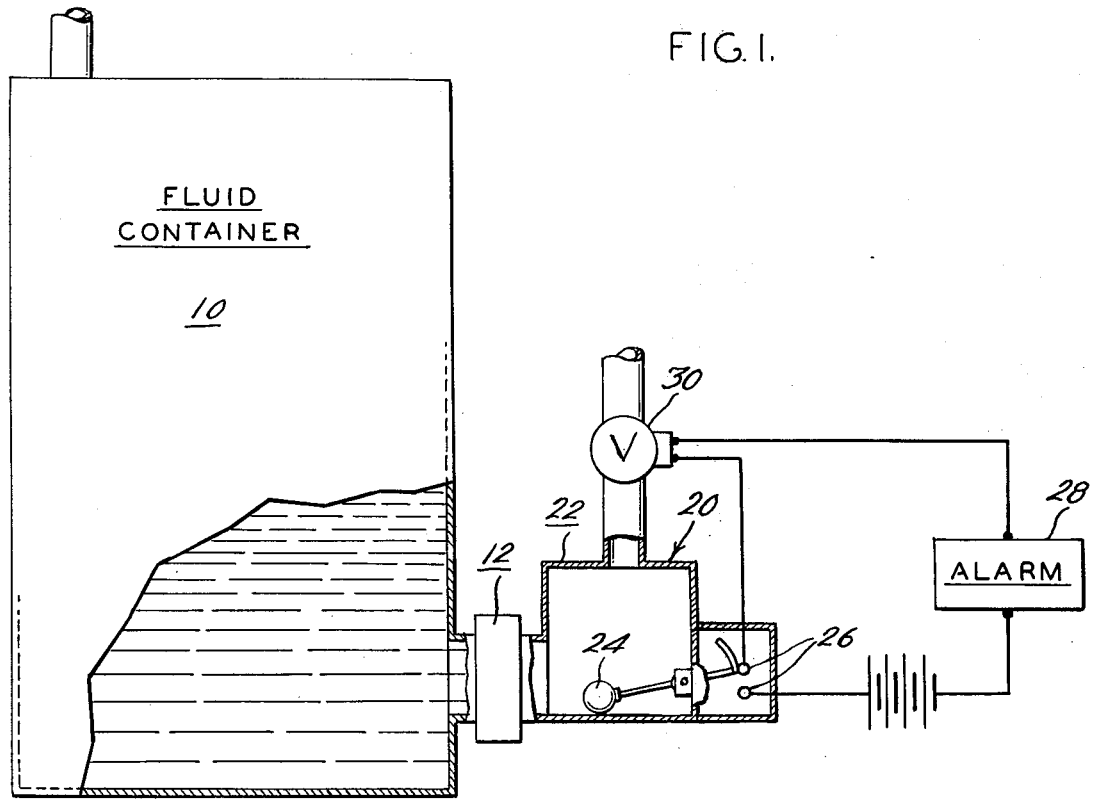
FIG.1.
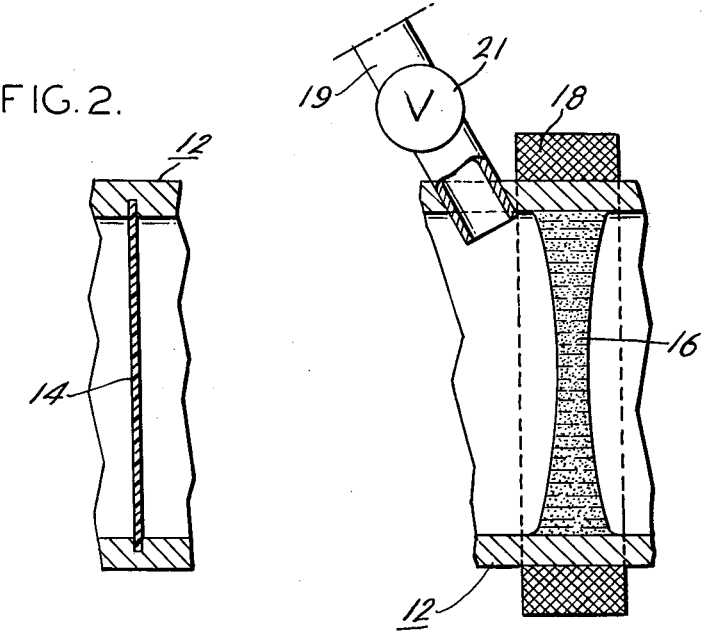
FIG.2.
FIG.3.

LIQUID CONTAMINATION DETECTOR

BACKGROUND OF THE INVENTION

The present invention relates generally to a system for detecting the presence of a contaminating fluid. More particularly, the present invention relates to a system for detecting the presence of hydrocarbons (such as petroleum products) in water or the presence of water in hydrocarbons. It is often necessary or desirable to detect the contamination of one fluid by another. Examples are hydrocarbons leaking into a line carrying boiler feed water, and water leaking into a petroleum plant feed stream. In either case contamination could cause serious damage to the equipment and loss of product. Also, in many instances the contamination of one fluid by another results in pollution of the environment.

SUMMARY OF THE INVENTION

In accordance with a preferred embodiment, a system is disclosed for detecting the presence of contaminating fluids among other, normal fluids. A barrier is positioned with one side in contact with the supply of fluids being checked. The barrier is soluble in the contaminating fluids, but insoluble in other, normal fluids in the fluid supply. A detector is positioned on the opposite side of the barrier, and detects the presence of fluids which have dissolved and penetrated the barrier.

In accordance with one disclosed embodiment of the invention, the barrier is a ferromagnetic fluid diaphragm wherein the base for the ferromagnetic fluid is soluble in the contaminating fluids. One advantage of this embodiment is that upon destruction of the fluid diaphragm by contaminating fluids, the diaphragm may be conveniently replaced by simply supplying more ferromagnetic fluid to the diaphragm.

BRIEF DESCRIPTION OF THE DRAWINGS

FIG. 1 illustrates schematically one embodiment of the present invention.

FIGS. 2 and 3 show different diaphragms which may be utilized with the present invention.

DESCRIPTION OF A PREFERRED EMBODIMENT

Referring to FIG. 1, there is illustrated one embodiment of the present invention. A fluid container 10, which may be a tank, pipe, or any other suitable container, holds fluid which is susceptible of being contaminated by another fluid. The container has a barrier 12 positioned with one side of the barrier in intimate contact with the fluids in the container. The barrier is a diaphragm of a type designed to be soluble in the contaminant but insoluble in the fluids normally in the container. If contaminants are present, they will dissolve the barrier and enter a detection system 20 which includes a separate container 22 having therein a float 24. Float 24 is mechanically coupled to electrical contacts 26 such that as liquid enters from container 10, element 24 floats and closes the contacts 26. The contacts 26 may actuate an alarm system 28, and may also close a normally open solenoid valve 30 to prevent the contents of container 10 from leaking out through the container 22.

The barrier may take any one of several forms, and may be the type illustrated in either FIG. 2 or FIG. 3. In the embodiment of FIG. 2 the barrier is a solid diaphragm which is soluble by the contaminating fluids, but is insoluble by the other, normal fluids in the container. In the embodiment wherein water is the normal fluid in the container, and the potential contaminants are hydrocarbons, the diaphragm 14 may be made of any suitable material which is soluble in hydrocarbons and insoluble in water. In the embodiment wherein hydrocarbons are the normal fluids and the potential contaminant is water the diaphragm may be made of any suitable material which is soluble in water and insoluble in hydrocarbons.

FIG. 3 shows a second embodiment of the invention wherein the barrier is a ferromagnetic fluid 16 which is held in place by an electromagnet 18. Such a ferromagnetic fluid is available under the tradename Ferrofluid from Ferrofluidics Corporation, Burlington, Mass. 01803. Ferrofluid consists of a base fluid which holds many tiny, ferromagnetic particles in suspension. These ferromagnetic fluids are available with different types of base fluids. In an embodiment wherein the container 10 normally holds water and the possible contaminants are hydrocarbons, a hydrocarbon based Ferrofluid may be ordered and utilized. In an embodiment where the container 10 normally hydrocarbons and the possible contaminant is water, a water based Ferrofluid may be ordered and utilized.

One advantage of the embodiment illustrated in FIG. 3 is that the apparatus might include a passage means, such as a tube 19 through which additional ferromagnetic fluid may be injected if contaminants dissolve the previous fluid diaphragm. In applications wherein it is expected that contaminants will be detected fairly frequently, this embodiment would be very useful, as the replacement of the diaphragm would entail merely opening valve 21, and inserting more ferromagnetic fluid into the magnetic field maintained by the coil for the suspension of the barrier therein.

Although at least one embodinent of the present invention has been described, the teachings of this invention will suggest many other embodiments to those skilled in the art.

The invention claimed is:

1. A system for detecting the presence of contaminating fluids while discriminating against the presence of other, normal fluids and comprising:
   a. means for holding a supply of fluids;
   b. a barrier means in said holding means and having one side in contact with the supply of fluids, said barrier means including a ferromagnetic fluid diaphragm wherein the base fluid of the ferromagnetic fluid is soluble by said contaminating fluids and is insoluble by other, normal fluids in said holding means; and
   c. means, positioned on the other side of said barrier means, for detecting the presence of a fluid which has dissolved and penetrated said barrier means.

2. A system as set forth in claim 1 and including a passage means, positioned adjacent to said ferromagnetic fluid diaphragm, for supplying more ferromagnetic fluid to the ferromagnetic fluid diaphragm, whereby in the event contaminating fluids dissolve the ferromagnetic fluid diaphragm and activate said detection means, more ferromagnetic fluid may be conveniently supplied to form a replacement diaphragm.

* * * * *